(12) United States Patent
Kim et al.

(10) Patent No.: US 9,970,779 B2
(45) Date of Patent: May 15, 2018

(54) SYSTEM AND METHOD FOR PROVIDING ROUTE GUIDANCE SERVICE FOR VISUALLY IMPAIRED PEOPLE

(71) Applicant: UNIST (ULSAN NATIONAL INSTITUTE OF SCIENCE AND TECHNOLOGY), Ulsan (KR)

(72) Inventors: Nam Hun Kim, Ulsan (KR); Dong Hwan Song, Seoul (KR); Yun Jae Lee, Seoul (KR); Kyoung In Beak, Jeollabuk-do (KR); Hyun Seo Nam, Ulsan (KR)

(73) Assignee: UNIST (ULSAN NATIONAL INSTITUTE OF SCIENCE AND TECHNOLOGY), Ulsan (KR)

(*) Notice: Subject to any disclaimer, the term of this patent is extended or adjusted under 35 U.S.C. 154(b) by 89 days.

(21) Appl. No.: 15/109,122

(22) PCT Filed: Dec. 24, 2014

(86) PCT No.: PCT/KR2014/012825
§ 371 (c)(1),
(2) Date: Jun. 29, 2016

(87) PCT Pub. No.: WO2015/102301
PCT Pub. Date: Jul. 9, 2015

(65) Prior Publication Data
US 2016/0327405 A1 Nov. 10, 2016

(30) Foreign Application Priority Data
Dec. 31, 2013 (KR) ........................ 10-2013-0169161

(51) Int. Cl.
*G06K 9/62* (2006.01)
*G01C 21/36* (2006.01)
(Continued)

(52) U.S. Cl.
CPC ..... *G01C 21/3629* (2013.01); *G01C 21/3423* (2013.01); *G01S 19/51* (2013.01); *G06F 19/3481* (2013.01); *G06Q 50/22* (2013.01)

(58) Field of Classification Search
CPC .... G06K 9/6247; G06K 9/62; G06K 9/00798; G06K 9/00805; G06F 3/016; G06F 1/163;
(Continued)

(56) References Cited

U.S. PATENT DOCUMENTS 5,495,534 A * 2/1996 Inanaga ................. H04S 1/005
381/310
5,687,136 A * 11/1997 Borenstein ............ A61H 3/061
367/116
6,069,585 A * 5/2000 Lanciaux ............... G01C 17/00
340/979

FOREIGN PATENT DOCUMENTS

JP 2005-308598 A 11/2005
KR 10-2009-0020857 A 2/2009
(Continued)

OTHER PUBLICATIONS

Japanese Patent Abstract (in English) of JP Pub. No. 2005-308598 A, Pub. Date Nov. 4, 2005.
(Continued)

*Primary Examiner* — Dalena Tran
(74) *Attorney, Agent, or Firm* — Barcelo, Harrison & Walker, LLP (57) ABSTRACT

The present invention relates to a method for providing a route guidance service for visually impaired people, the method comprising the steps of: when a predetermined application is selected through a user input, transmitting a request for a route guidance service together with location information acquired through the GPS of a user terminal simultaneously with execution of the selected application; servicing, by a route guidance server, search path informa- (Continued)

tion corresponding to an input destination on the basis of the location information received from the user terminal according to the route guidance service request from the user terminal; broadcasting, by the user terminal, an inquiry signal through a Bluetooth device search request, identifying an earphone by a device which transmits a response signal to the broadcasted inquiry signal, and performing paging with the identified earphone; and recognizing a user's walking direction on the basis of the search path information through outputting a signal by gyro sensors attached to both sides of the earphone according to a user's movement, converting the recognized result into a guidance sound according to a route guidance service rule, and outputting the guidance sound to the earphone.

5 Claims, 9 Drawing Sheets

(51) Int. Cl.
    *G06Q 50/22*         (2018.01)
    *G06F 19/00*         (2018.01)
    *G01C 21/34*         (2006.01)
    *G01S 19/51*         (2010.01)

(58) Field of Classification Search
    CPC ......... G06F 3/015; G06F 3/038; G01C 21/26; G01C 21/34; G01S 5/0009
    USPC ............. 701/487; 706/20, 25, 934; 348/116; 361/679.03
    See application file for complete search history.

(56) References Cited

FOREIGN PATENT DOCUMENTS

| KR | 10-2011-011799 A | 2/2011 |
| KR | 10-2011-0120626 A | 11/2011 |
| KR | 101343550 B1 | 12/2013 |

OTHER PUBLICATIONS

Korean Patent Abstract (in English) of KR Patent. No. 10-1343550 B1, dated Dec. 13, 2013, downloaded Jun. 21, 2016, from http://engpat.kipris.or.kr/.
Korean Patent Abstract (in English) of KR Pub. No. 10-2009-0020857 A, Pub. Date Feb. 27, 2009, downloaded Jun. 29, 2016.
Korean Patent Abstract (in English) of KR Pub. No. 10-2011-0011799 A, Pub. Date Feb. 9, 2011, downloaded Jun. 29, 2016.
Korean Patent Abstract (in English) of KR Pub. No. 10-2011-0011799 A, Pub. Date Feb. 9, 2011, downloaded Jun. 21, 2016 from http://engpat.kipris.or.kr/.
Korean Patent Abstract (in English) of KR Pub. No. 10-2011-0120626, dated Nov. 4, 2011, downloaded Jun. 29, 2016.

\* cited by examiner

| number of test / test subject | 1st time | 2nd time | 3rd time | 4th time | 5th time | 6th time | 7th time | 8th time | 9th time | 10th time | 11th time | 12th time | number of correction |
|---|---|---|---|---|---|---|---|---|---|---|---|---|---|
| 1 | ○ | ○ | * | ○ | * | ○ | * | ○ | ○ | ○ | ○ | ○ | 9 |
| 2 | ○ | ○ | ○ | ○ | ○ | ○ | ○ | ○ | ○ | ○ | ○ | ○ | 12 |
| 3 | ○ | ○ | ○ | ○ | ○ | ○ | ○ | ○ | ○ | ○ | ○ | ○ | 11 |
| 4 | ○ | ○ | ○ | * | ○ | * | ○ | ○ | * | ○ | * | * | 7 |
| 5 | ○ | ○ | ○ | * | ○ | ○ | ○ | * | ○ | * | ○ | ○ | 9 |
| 6 | ○ | ○ | ○ | ○ | ○ | ○ | ○ | ○ | ○ | ○ | ○ | * | 11 |
| 7 | ○ | ○ | ○ | ○ | ○ | ○ | ○ | * | ○ | ○ | ○ | ○ | 12 |
| 8 | * | ○ | ○ | ○ | ○ | ○ | ○ | ○ | ○ | ○ | ○ | ○ | 9 |
| total number of correction | 7 | 8 | 7 | 6 | 6 | 7 | 7 | 6 | 6 | 7 | 7 | 6 | 80 |

| number of test / test subject | 1st time | 2nd time | 3rd time | 4th time | 5th time | 6th time | 7th time | 8th time | 9th time | 10th time | 11th time | 12th time | number of correction |
|---|---|---|---|---|---|---|---|---|---|---|---|---|---|
| 1 | ○ | ○ | * | ○ | * | ○ | * | ○ | ○ | ○ | ○ | ○ | 9 |
| 2 | ○ | ○ | ○ | * | * | * | ○ | * | * | * | ○ | ○ | 12 |
| 3 | ○ | ○ | ○ | ○ | ○ | * | ○ | ○ | ○ | * | ○ | ○ | 11 |
| 4 | * | ○ | ○ | ○ | ○ | ○ | ○ | ○ | ○ | ○ | * | ○ | 7 |
| 5 | ○ | * | ○ | * | * | ○ | * | ○ | ○ | ○ | ○ | ○ | 9 |
| 6 | ○ | * | ○ | ○ | * | ○ | * | ○ | ○ | * | ○ | * | 11 |
| 7 | * | * | ○ | * | ○ | * | * | * | * | * | ○ | * | 12 |
| 8 | ○ | ○ | ○ | ○ | ○ | ○ | ○ | ○ | ○ | ○ | ○ | ○ | 9 |
| total number of correction | 6 | 4 | 7 | 5 | 4 | 5 | 4 | 5 | 6 | 4 | 7 | 6 | 80 |

SYSTEM AND METHOD FOR PROVIDING ROUTE GUIDANCE SERVICE FOR VISUALLY IMPAIRED PEOPLE

CROSS-REFERENCE TO RELATED APPLICATIONS

This application claims priority from Korean Patent Application No. 10-2013-0169161, filed on Dec. 31, 2013, in the Korean Intellectual Property Office. The entire contents of said application are incorporated herein by reference.

BACKGROUND OF THE DISCLOSURE

1. Technical Field

The present invention relates to a route guidance service by a mobile terminal and an earphone for visually impaired people equipped with a gyro sensor using near field communication.

2. Background Art

In general, when visually impaired people walk down the street or move to another place, they move while sensing obstacles, etc. in walking direction using sticks.

In this case, the visually impaired people can walk more easily along guidance blocks installed on the ground or roads. However, even if such guidance blocks are installed, in the case of an obstacle placed at a predetermined height or greater from the ground or of various situations that may occur abruptly while moving, there are problems that the visually impaired people cannot promptly sense this case.

Figure 1:
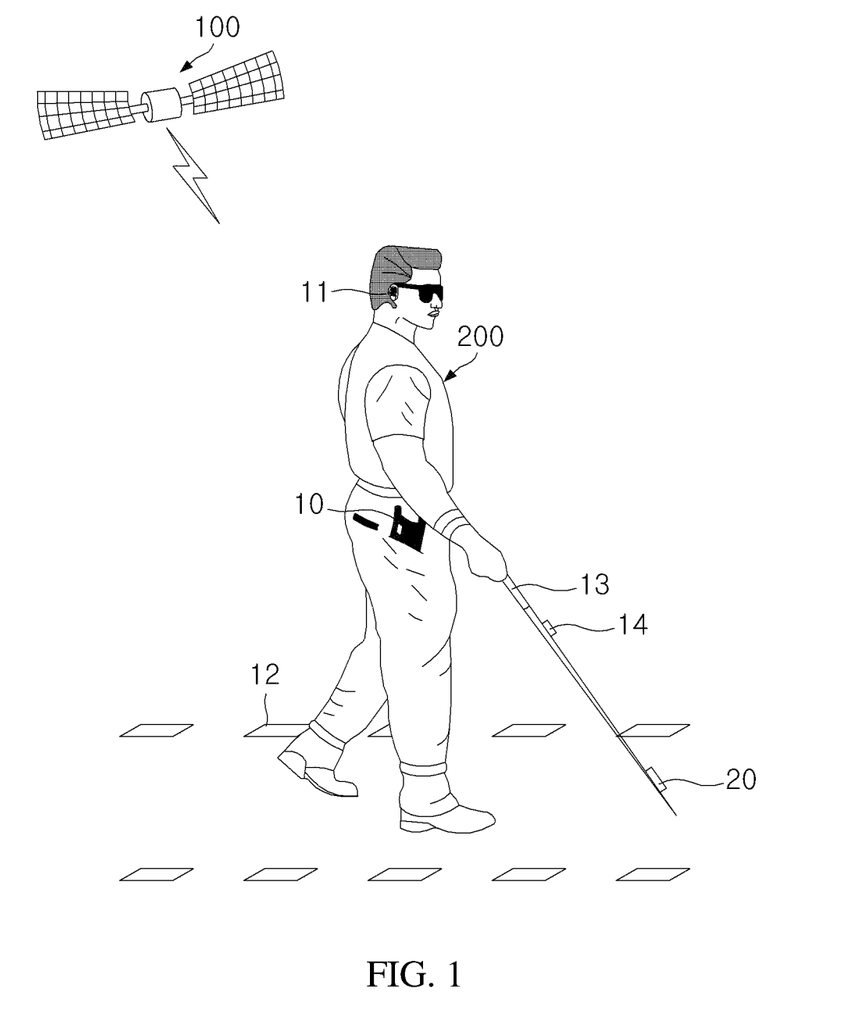
FIG. 1 and FIG. 2 are illustrations for a conventional route guidance service system for visually impaired people.
Figure 2:
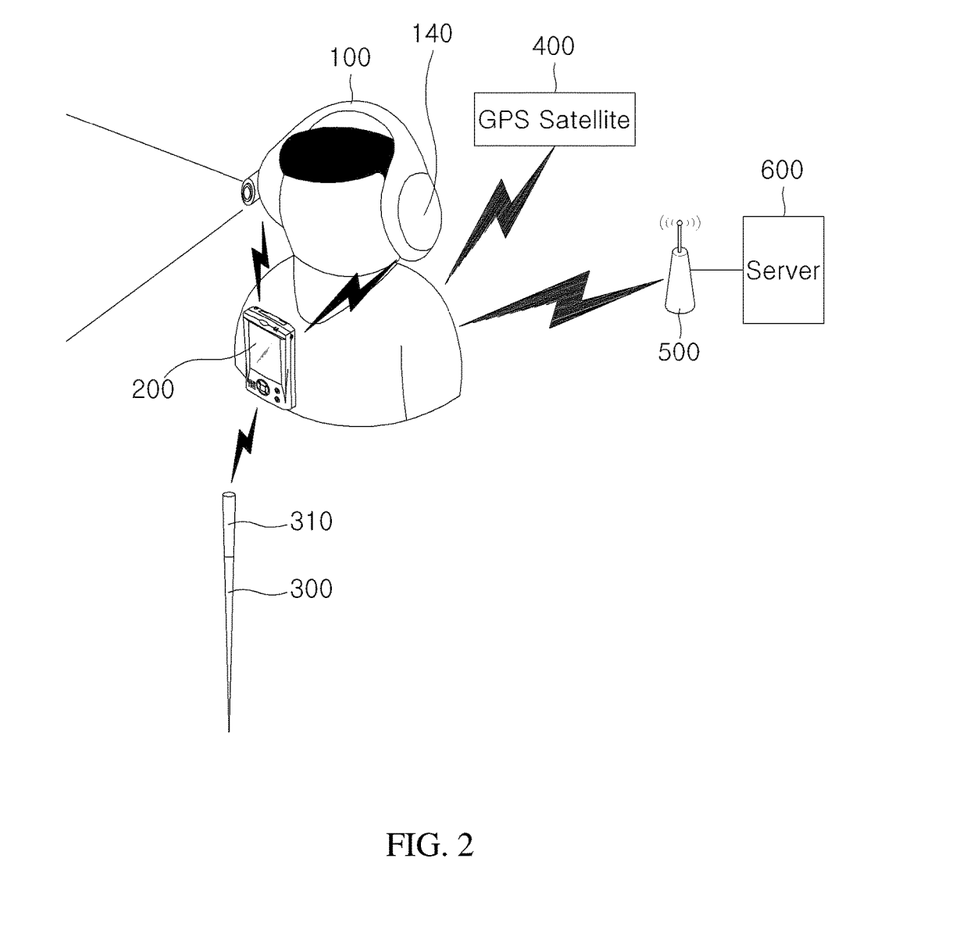

Also, as described in the prior arts below and FIG. 1 and FIG. 2 corresponding thereto, while the existing route guidance and navigation system provided only by vision are converted into voice, with the voice guidance alone, numerous information which were shown visually are omitted, and thereby an accurate walking direction cannot be provided to the visually impaired people.

Furthermore, with the voice guidance, information which is visually simple may be delivered for a relatively long time, and thereby an instant information delivery cannot be made.

The limitation of the information delivery may act as a great dangerous element to the visually impaired people who actually walk down the street.

Figure 3:
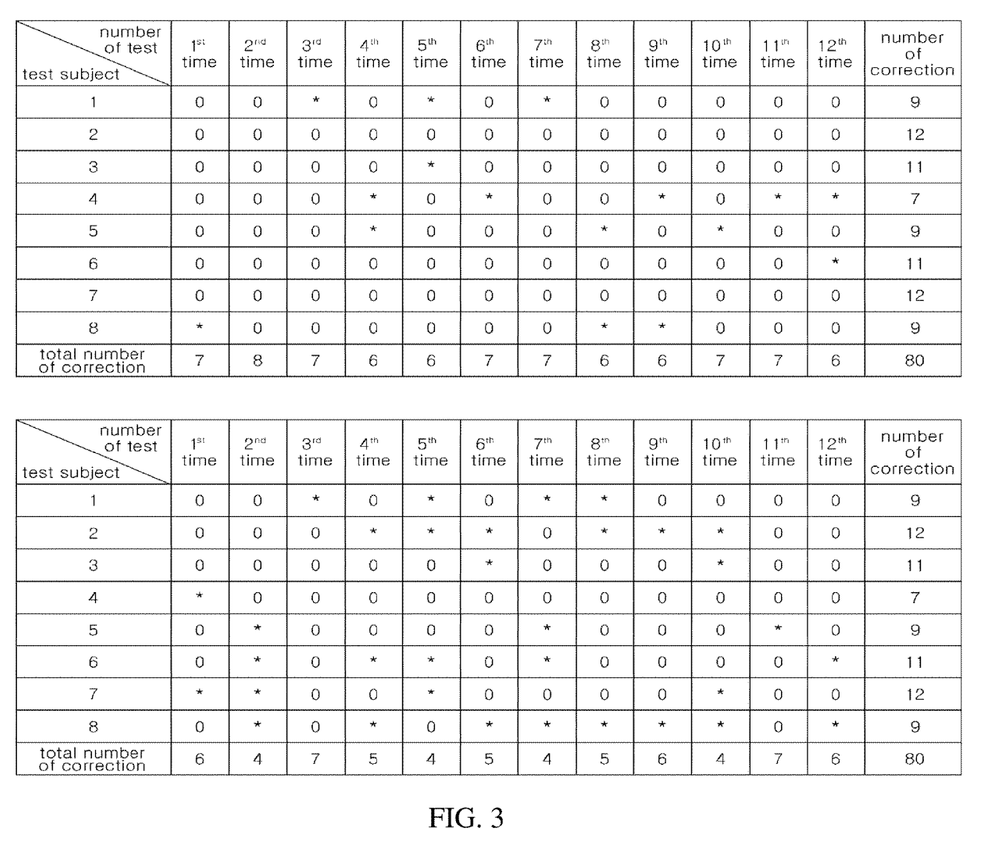
FIG. 3 is a table showing a limit of vibration/tactile sense stimulus of a conventional haptic navigation system for visually impaired people.

Meanwhile, as compared in the Table of FIG. 3, in the case of stimulus by means of vibration/tactile sense, as a result of existing haptic navigation for visually impaired people, the accuracy in recognition for vibration stimulus of a test subject is merely 65-85%, which is an impossible level for the visually impaired people to use during their actual walking.

Additionally, a threshold for the vibration stimulus is rapidly increased, and thereby sensitivity is easily decreased. Thus, there is a limit to continuously use the vibration stimulus.

PRIOR ARTS

Patent Documents

Korean Patent Laid-Open No. 10-2011-0120626
Korean Patent Laid-Open No. 10-2009-0020857
Korean Patent Laid-Open No. 10-2011-0011799

SUMMARY OF INVENTION

Technical Task

The present invention provides a technology capable of providing an instant direction recognition service more precisely and accurately only with the sound through a route guidance service with a movement direction of visually impaired people applied, by interworking, with a user terminal through a Bluetooth communication, an earphone to which a gyro sensor, which senses the user's movement direction so that the visually impaired people accurately and safely walk to a target spot while recognizing an object ahead, is attached, adaptively converting into a guidance sound according to a route guidance service rule, and outputting the guidance sound to the earphone.

Technical Means for Achieving Technical Task

According to one aspect of the present invention, the present invention relates to a method for providing a route guidance service for visually impaired people, which includes the steps of: when a predetermined application is selected through a user input, transmitting a request for a route guidance service together with location information acquired through the GPS of the user terminal simultaneously with execution of the selected application; servicing, by a route guidance service server, search path information corresponding to an input destination on the basis of the location information received from the user terminal according to the route guidance service request from the user terminal; broadcasting, by the user terminal, an inquiry signal through a Bluetooth device search request, identifying an earphone by a device which transmits a response signal to the broadcasted inquiry signal, and performing paging with the identified earphone; and recognizing a user's walking direction on the basis of the search path information through outputting a signal by gyro sensors attached to both sides of the earphone according to a user's movement, converting the recognized result into a guidance sound according to a route guidance service rule, and outputting the guidance sound to the earphone.

According to another aspect of the present invention, the present invention relates to a system for providing a route guidance service for visually impaired people, which includes: a user terminal which transmits, when a predetermined application is selected through a user input, a request for a route guidance service together with location information acquired through the GPS of the user terminal simultaneously with execution of the selected application; a route guidance service server which services search path information corresponding to an input destination on the basis of the location information received from the user terminal according to the route guidance service request from the user terminal; and an earphone which transmits a response signal to a broadcasted inquiry signal through a Bluetooth device search request at the user terminal, performs paging with the user terminal, and senses and outputs a user's movement through gyro sensors attached to both sides thereof.

Effect of the Invention

The present invention instantly provides a general situation of a travelling path acoustically only through a Bluetooth earphone during the route guidance service, so that no additional device is necessary, which is advantageous for securing low costs. Also, the present invention exhibits an effect of providing an instant direction recognition service more precisely and accurately only with the sound through the route guidance service to which the movement of visually impaired people is applied by using a gyro sensor of an earphone.

DETAILED DESCRIPTION

Mode for Carrying Out the Invention

Hereinafter, preferred embodiments according to the present invention will be explained in detail with reference to the accompanying drawings. While specific details such as components are described in the following description, they are given only to help comprehensive understanding of the present invention. Therefore, it is clearly to be understood to those skilled in the art that changes or modifications can be made to the present invention within the scope and spirit of the present invention.

The present invention relates to a navigation system for visually impaired people, and more specifically provides a technology which interworks, with a user terminal through a Bluetooth communication, an earphone to which an electronic compass and a gyro sensor are attached so that the visually impaired people accurately and safely walk to a target spot while recognizing an object ahead, transmits a request for a route guidance service together with location information acquired through the GPS of the user terminal simultaneously with execution of an application specialized for the route guidance service for the visually impaired people, provides through a route guidance service server search path information corresponding to an input destination on the basis of the location information received from the user terminal, recognizes a user's walking direction on the basis of the search path information through the gyro sensor of the earphone paged through the Bluetooth communication, adaptively converts the recognized result into a guidance sound according to a route guidance service rule, and outputs the guidance sound to the earphone, thereby instantly providing a general situation of a travelling path acoustically only through a Bluetooth earphone during the route guidance service. Accordingly, no additional device is necessary, which is advantageous for securing low costs. Also, the present invention provides a technology capable of providing an instant direction recognition service more precisely and accurately only with the sound through the route guidance service to which the movement of the visually impaired people is applied by using the gyro sensor of the earphone.

Additionally, nodes of the user terminal according to an embodiment of the present invention may include all information communication equipment and multimedia equipment, etc., such as a digital broadcasting terminal, a Personal Digital Assistant (PDA), a smart phone, a tablet PC, an IPad, 3G and 4G Long Term Evolution (LTE) terminal, for example, International Mobile Telecommunication 2000 (IMT-2000) terminal, Wideband Code Division Multiple Access (WCDMA) terminal, Global System For Mobile Communication Packet Radio Service (GSM/GPRS) and Universal Mobile Telecommunication Service (UMTS) service, and GPS using satellites. However, a skilled person in the art would easily understand that the constitution according to an embodiment described herein may be applied even to fixed terminals such as a digital TV, a desktop computer, etc., except the case which is applicable only to portable terminals.

Hereinafter, the method for providing the route guidance service for visually impaired people according to one embodiment of the present invention will be explained in detail with reference to FIG. 4 to FIG. 7.

Figure 4:
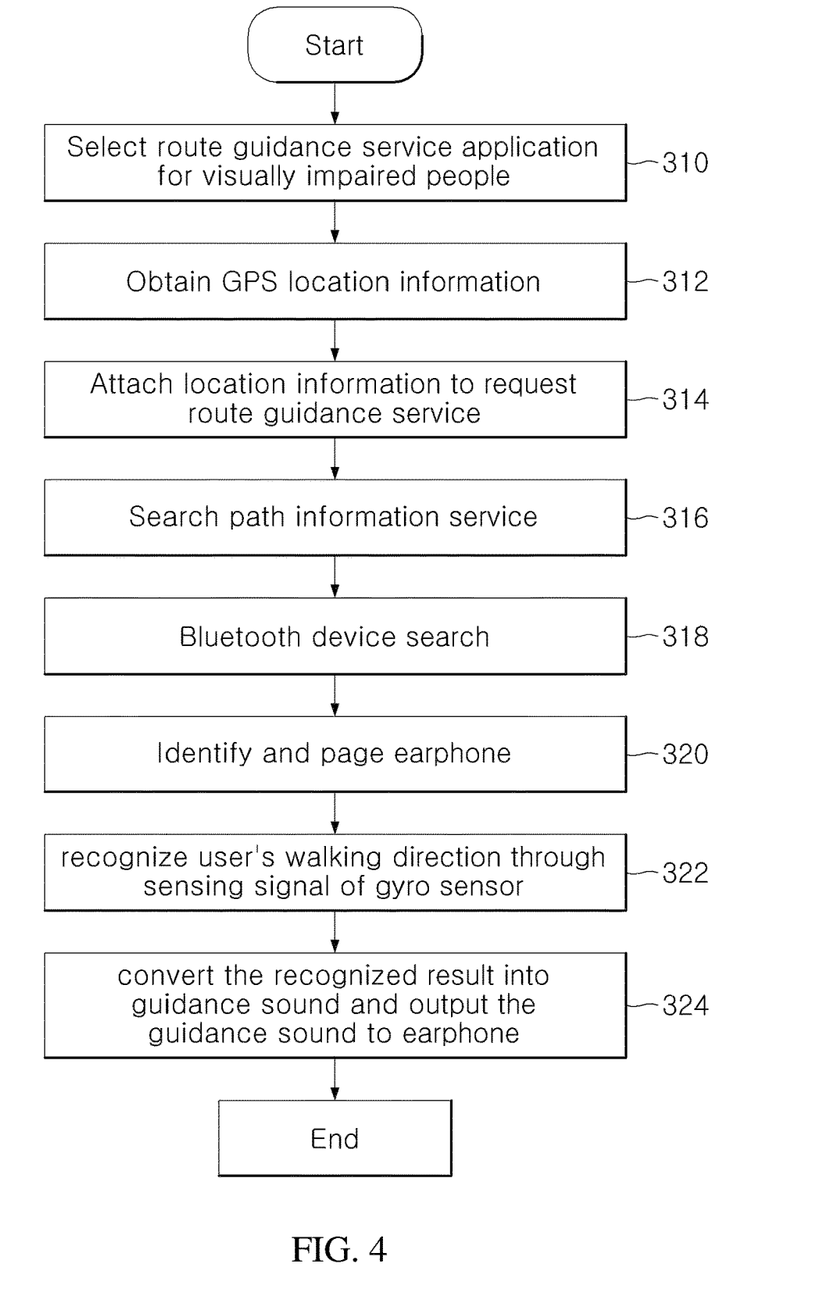
FIG. 4 is an overall flow chart illustrating a method for providing a route guidance service for visually impaired people according to one embodiment of the present invention.

First, FIG. 4 is an overall flow chart illustrating a method for providing a route guidance service for visually impaired people according to one embodiment of the present invention.

Referring to FIG. 4, first, in step 310, a predetermined application is selected through a user input. The application selected from the user is an application specialized for the route guidance service for visually impaired people, and in order for the visually impaired people to easily use the application even in the user terminal equipped with a touchscreen, a menu or an item corresponding thereto is disposed on a corner in a display unit in which the application is activated, or the menu or item is made to operate by the voice recognition, so that the application is serviced with high accessibility by the visually impaired people.

In step 312, the Global Positioning System (GPS) information is acquired based on the location based service (LB S) simultaneously with the execution of the selected application. The acquired GPS information means a current location of the user terminal, which is the information updated in real time corresponding to the movement when the user terminal moves.

In step 314, a specific path data service request based on the location information of the user terminal acquired in step 312 is made, and a request for the route guidance service is transmitted together with the location information acquired through the GPS of the user terminal.

In step 316, the search path information corresponding to the input destination is serviced, by the route guidance service server, on the basis of the location information received from the user terminal according to the route guidance service request from the user terminal.

In this case, the user terminal displays in the display unit travelling path information corresponding to the destination which is continuously serviced in real time through the route guidance service server interworked through the network. Meanwhile, a mode of the corresponding user terminal is converted into a sleep mode and performs a Bluetooth device search for the guidance through the earphone to which the sensor is attached.

In other words, in step 318, when the inquiry signal is broadcasted through the Bluetooth device search request at the user terminal, the response signal to the broadcasted inquiry signal is transmitted, the earphone for performing the voice route guidance service is identified at a plurality of devices transmitting the response signal, and the paging with the earphone identified is performed according to a Bluetooth protocol for near field communication.

Afterwards, in step 322, the user's walking direction on the basis of the search path information is recognized through a signal output of the gyro sensors attached to both sides of the earphone according to the movement of the user.

In step 324, the recognized result is converted into the guidance sound according to the route guidance service rule and the guidance sound is output to the earphone.

Here, the recognized result is acquired from the comparison with the user's walking direction data acquired from the gyro sensor of the earphone which is paged through the Bluetooth communication on the basis of the search path information to a specific destination provided from the route guidance service server to the user terminal. The guidance sound is controlled so that the result of comparison with the user's walking direction data corresponds to the cycle determined according to a rotation angle for each type of direction shifting position on the basis of the search path information to selectively output the guidance sound to left side or right side of the earphone.

In this case, the control of the guidance sound output cycle according to the rotation angle is derived from Equation 1 below.

$$N(\text{Hz}) = roundn\left(\frac{\Theta}{10}\right) \qquad \text{Equation 1}$$

(Here, N refers to frequency of beep sound output, and θ refers to a difference angle between a walking path and a current azimuth).

The type of direction shifting position includes nodes which are branched into at least two present in a travelling path where the direction shifting occurs during the route guidance service.

Figure 5:
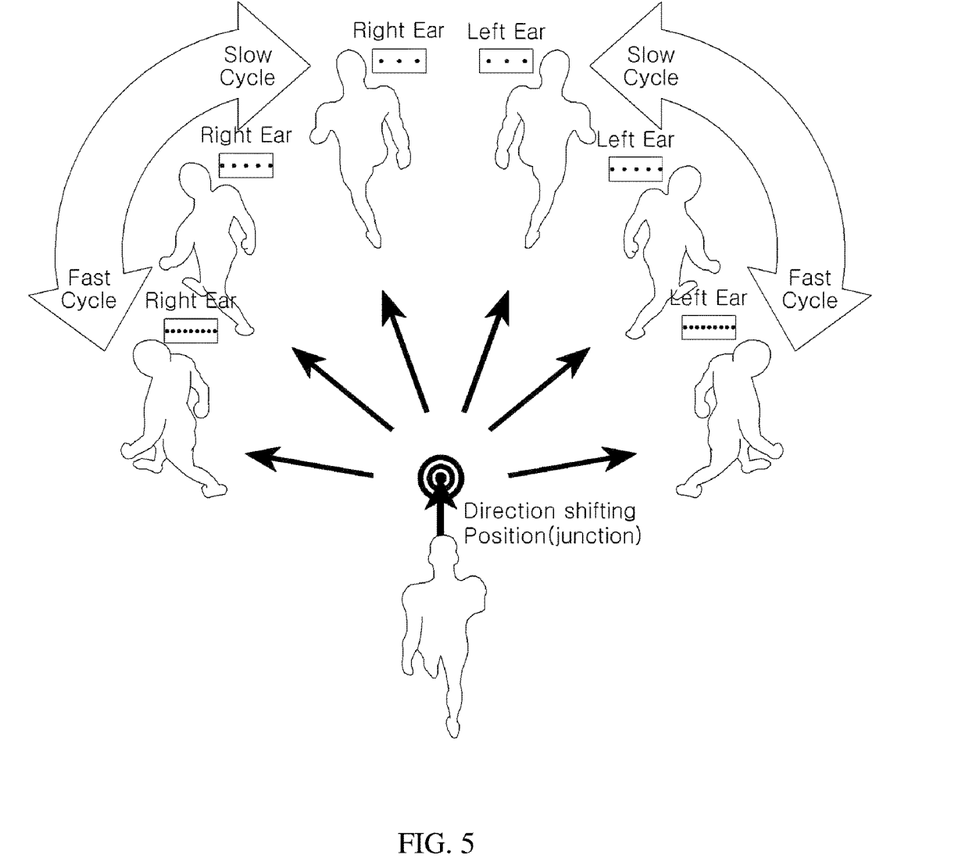
FIG. 5 is an illustration for a guidance sound control at a junction, in the method for providing a route guidance service for visually impaired people according to one embodiment of the present invention.

More specifically, referring to FIG. 5, first, FIG. 5 is an illustration for a guidance sound control at a junction, in the method for providing a route guidance service for visually impaired people according to one embodiment of the present invention. After the destination is selected, the user terminal becomes the sleeping mode, and the guidance starts through the earphone to which the sensor is attached. Afterwards, when the gyro sensors at both sides of the earphone recognize the user's current walking direction, and outputs and transmits the sensed signal to the user terminal, the user terminal compares the path to be walked and data of the current direction based on the search path information which is serviced from the route guidance service server at to send an acoustic signal to the earphone.

In this case, as illustrated in FIG. 5, as to the acoustic signal, as the rotation angle gets greater according to the walking direction and path angles at the junction, the signal with a high cycle (a fast cycle) is output. Additionally, the signal is output only to the left side or right side of the earphone according to the rotation direction.

Additionally, when further rotation occurs than the consistent direction, the signal sound is slowly output to the opposite side of the earphone, allowing the direction to be re-controlled. When the direction is consistent and the guidance should be made to go straight, both sides of the earphone recognize a specific signal for going straight and maintain the straight direction silently. In the same manner, even in case of deviating the path from the travelling direction, the correction to the direction with an acoustic signal may be instantly made to the user upon deviation.

Accordingly, the present invention does not separately apply a standard for determining a complex junction to the route guidance voice serviced from the route guidance service server, but simply corresponds thereto with attribute grant and directly senses the user's movement direction based thereon, thereby capable of providing more intuitive route guidance. Due to this, in the complex junction where there exist paths whose rotation types are similar to each other, it is possible to provide the path guidance service capable of providing more accurate path guidance.

Figure 6:
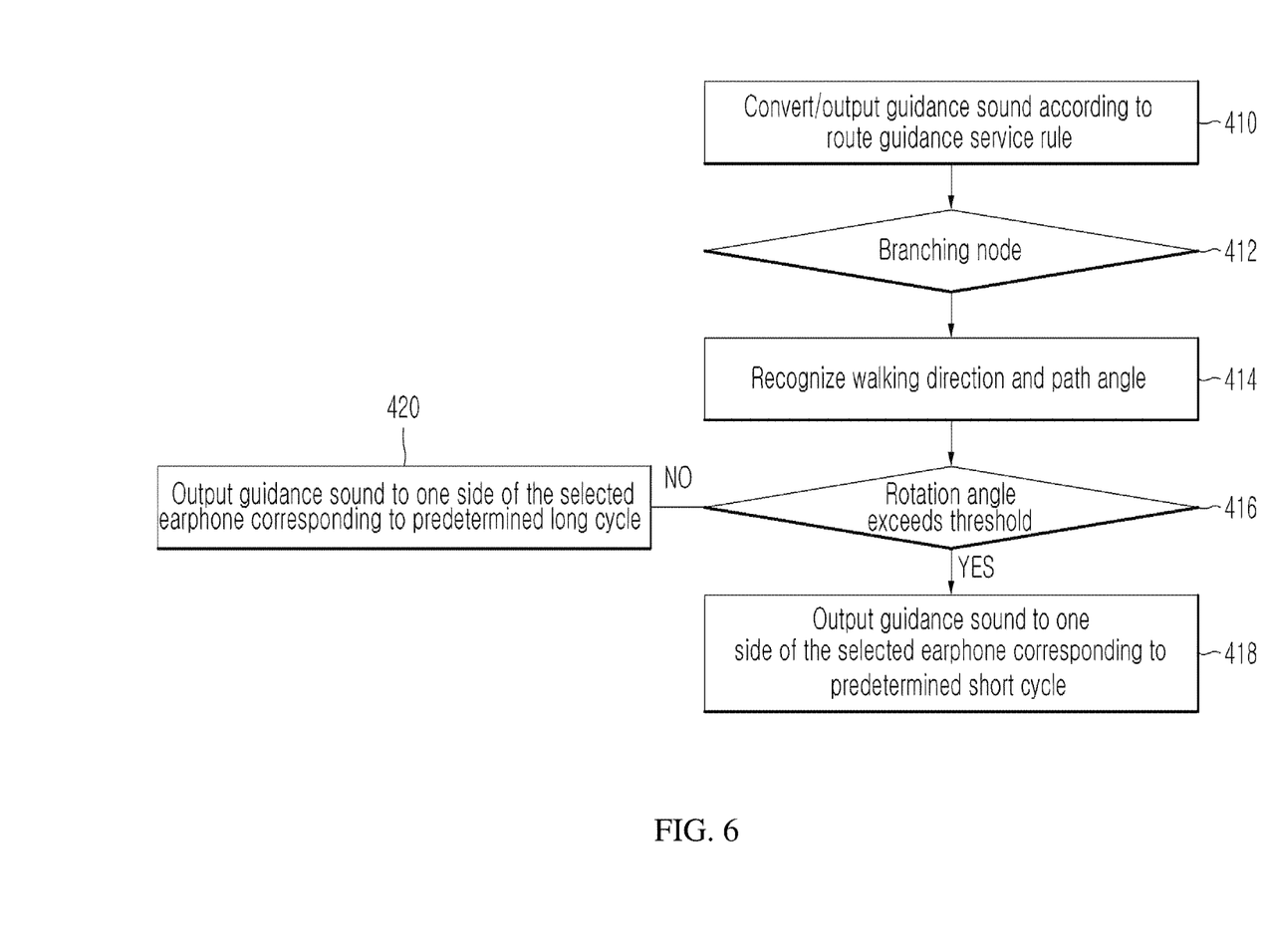
FIG. 6 is a flow chart relating to the guidance sound control at the junction, in the method for providing a route guidance service for visually impaired people according to one embodiment of the present invention.

Next, FIG. 6 is a flow chart illustrating the entire operation of FIG. 5. Referring to FIG. 6, first, in step 410, the path guidance of the user who is walking is continuously performed in real time to the corresponding destination through the conversion and output of the guidance sound according to the route guidance service rule.

In step 412, whether there is the junction node on the path is checked. As a result of checking, when there is the junction, in step 414, the angle at which the walking user needs to rotate at the junction is recognized based on the destination.

In step 416, whether the recognized rotation angle exceeds a threshold is checked. When the recognized rotation angle exceeds the threshold, go to step 418, or otherwise, go to step 420 to perform the corresponding operation.

Accordingly, the output cycle of the guidance sound is controlled correspondingly depending on whether the predetermined rotation angle exceeds a threshold. When the rotation angle exceeds the threshold, the guidance sound is continuously output at a predetermined short cycle to either a left side or right side of an earphone. When the rotation angle is below the threshold, the guidance sound is continuously output at a predetermined long cycle to the side opposite the side of the case of exceeding the threshold.

Figure 7:
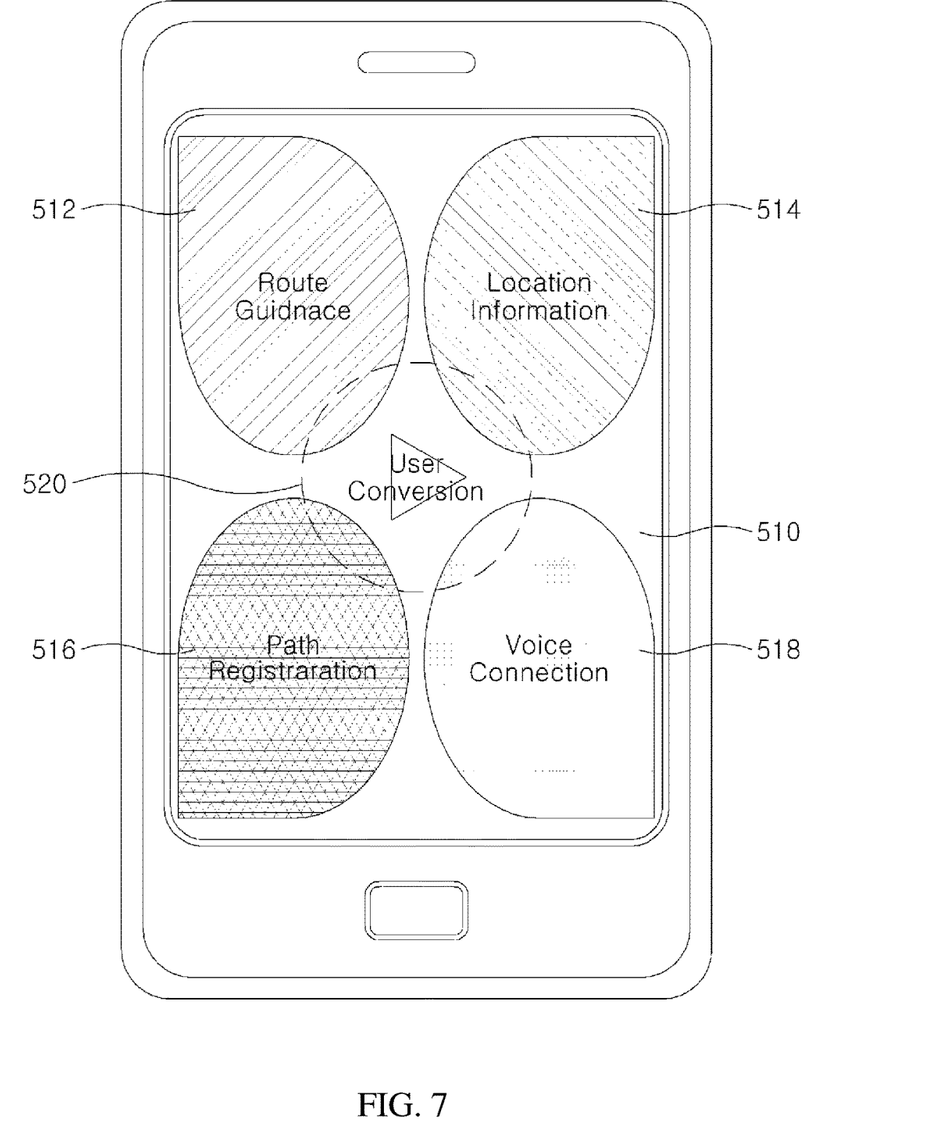
FIG. 7 is a screen illustration of an application to which a technology of providing a route guidance service for visually impaired people according to one embodiment of the present invention is applied.

Meanwhile, in the method for providing the route guidance service for visually impaired people to which the present invention applies, as illustrated in FIG. 7, the application provided at the user terminal disposes the menu at the corner so as to be easily used as the UI design specialized for visually impaired people in a home screen 510. The contents of each menu are as follows:

Route Guidance Menu 512

The route guidance menu performs a route guidance function to a determined destination, which is the most important function of sound view. The user selects the menu and sets the destination with a simple operation such as voice recognition, etc. Afterwards, the route guidance through the acoustic signal together with the voice guidance is executed.

Additionally, when the route guidance is executed, the user's location information and destination are instantly delivered and provided to determined people such as guardian and family, etc.

Location Information Menu 514

The location information menu provides the user's current location information with voice, and also provides surrounding information of the current location and information on traffic, facilities, etc. It is possible to use the corresponding function in combination even during the use of the route guidance function.

Path Registration Menu 516

The path registration menu allows the user to directly register a path to the destination. Accordingly, the menu allows the user to directly register a path which the user often walks or a specific path to the destination.

Voice Connection Menu 518

The voice connection menu instantly connects the user to the guardian or family through data communication. The guardian or family connected transmits in real time the user's location information as shown in the drawing above and image information using a camera of a smartphone. Additionally, the menu allows the guardian or family to set the path and destination remotely.

User Conversion Menu 520

When a user interrupt occurs by exceeding the predetermined time at a specific area among the areas in which the menu item list is marked, the driving mode of the user terminal is converted into the mode for non-visually impaired people, and performs a menu service corresponding to the converted mode.

In other words, the user conversion menu is executed only when pressing the menu for 3 to 5 seconds. After the execution, an additional menu for non-visually impaired people is shown. In the corresponding menu, it is possible to execute an additional function such as setting detailed surroundings, path, location, etc. Additionally, the menu allows the setting and operation for the guardian or family of non-visually impaired people possible.

As such, the application provided by the present invention has a plurality of divided areas 512, 514, 516, 518 and 520. In each of the divided areas, a menu item list (route guidance, location information, path registration, voice connection and user conversion) in which the corresponding item is formed is displayed. A link is set to a relevant page providing the service relate with the item (route guidance, location information, path registration, voice connection and user conversion) formed in the divided areas 512, 514, 516, 518 and 520. When selecting the corresponding menu item, the screen moves to the page link set to provide the predetermined service.

As stated above, the method for providing the route guidance service for visually impaired people according to one embodiment of the present invention is explained.

Hereinafter, a system for providing the route guidance service for visually impaired people according to one embodiment of the present invention will be explained in detail with reference to FIG. 8 and FIG. 9.

Figure 8:
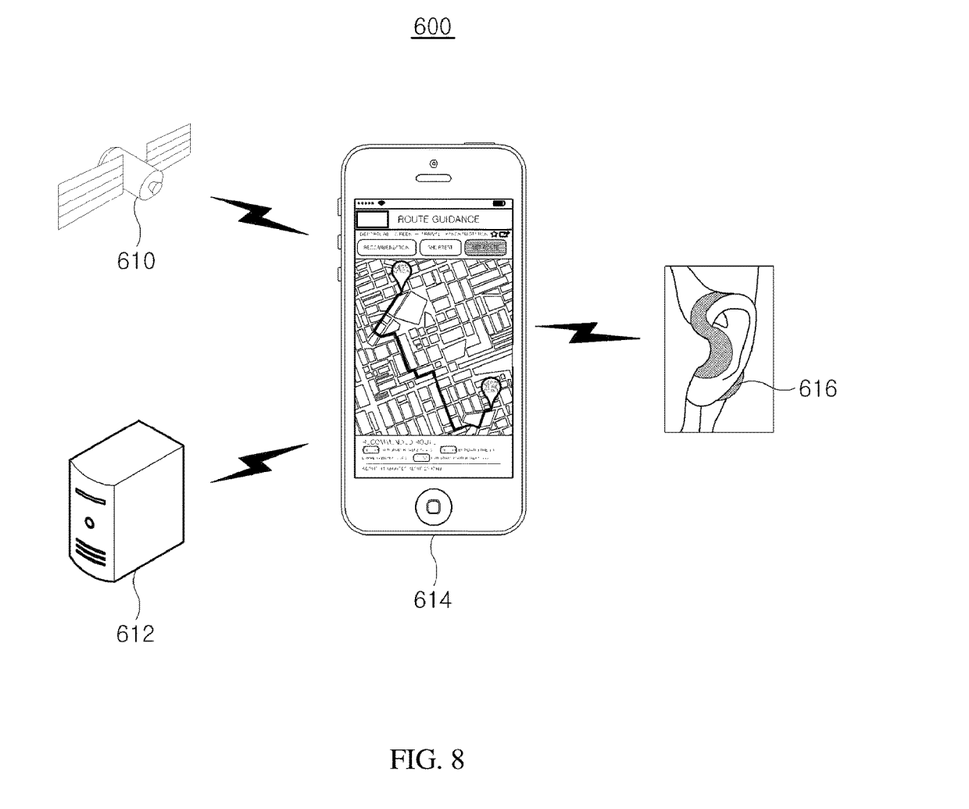
FIG. 8 is an illustration system for providing a route guidance service for visually impaired people according to one embodiment.

First, FIG. 8 is a schematic block diagram illustrating the system for providing the route guidance service for visually impaired people according to one embodiment of the present invention.

Referring to FIG. 8, the system 600 to which the present invention applies includes a GPS 610, a route guidance service server 612, a user terminal 614 and an earphone 616.

The user terminal 614 transmits, when a predetermined application is selected through a user input, a request for a route guidance service together with location information acquired through the GPS of the user terminal simultaneously with execution of the selected application.

The route guidance service server 612 services search path information corresponding to an input destination on the basis of the location information received from the user terminal 614 according to the route guidance service request from the user terminal 614.

The earphone 616 transmits a response signal to the inquiry signal broadcasted through the Bluetooth device search request at the user terminal 614, performs the paging with the user terminal 614, and senses and outputs the user's movement through the gyro sensors attached to the both sides of the earphone.

Figure 9:
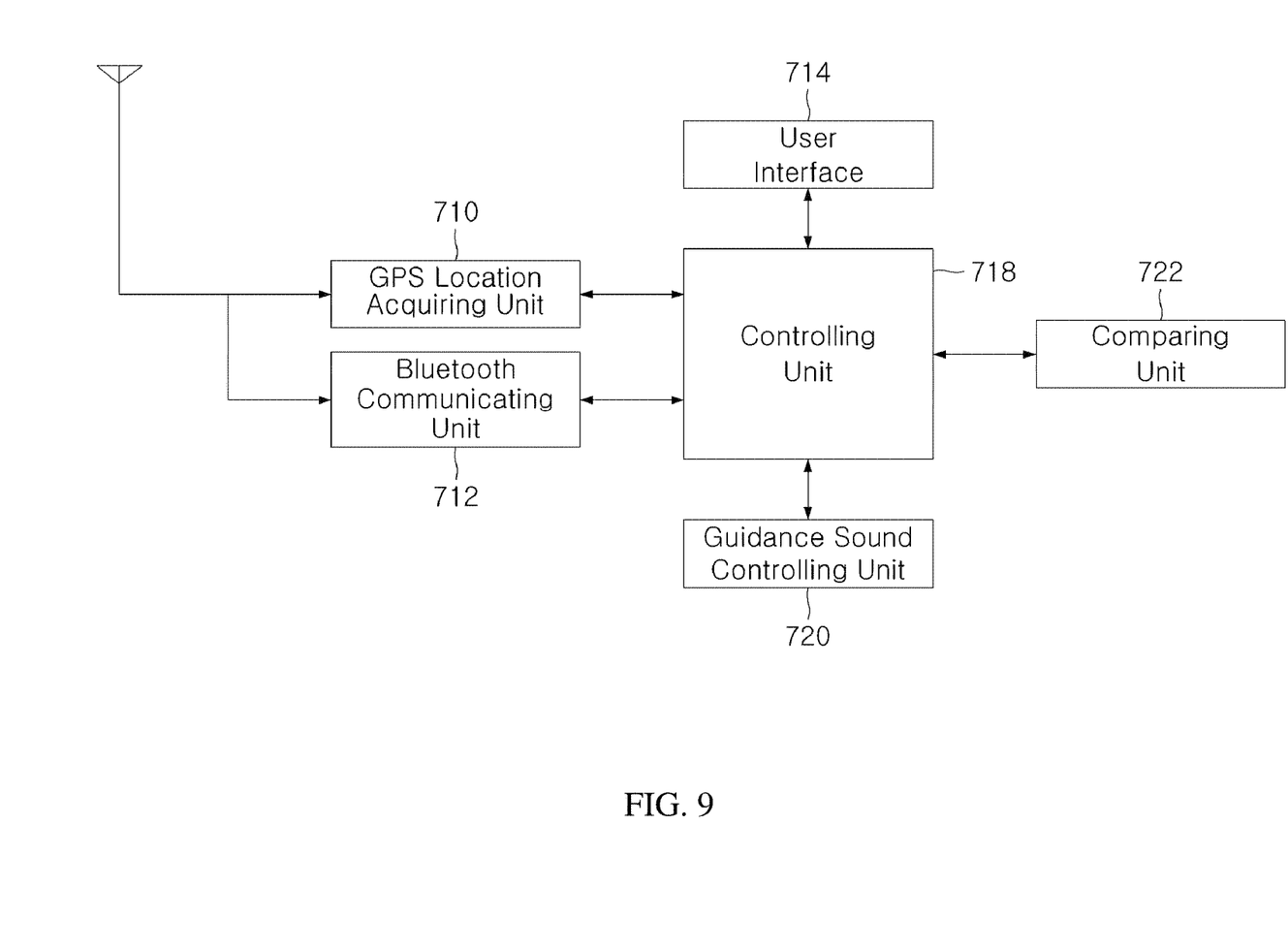
FIG. 9 is a block diagram illustrating a user terminal in the system for providing a route guidance service for visually impaired people according to one embodiment.

Here, referring to FIG. 9, FIG. 9 illustrates the constitution of the user terminal 700 in the system for providing the route guidance service for visually impaired people according to one embodiment of the present invention, which includes a GPS location acquiring unit 710, a Bluetooth communicating unit 712, a user interface 714, a controlling unit 718, a guidance sound controlling unit 720, a comparing unit 722 and a wireless communicating unit 724.

Main parts of the user terminal are as below.

The controlling unit 718 recognizes the user's walking direction through the sensing signal of the gyro sensor of the earphone paged through the Bluetooth communication based on the search path information serviced through the interworked route guidance service server, and converts the recognized result into the guidance sound according to the route guidance service rule and outputs the guidance sound to the earphone.

The controlling unit 718 acquires the recognized result by performing a comparison through the comparing unit 722 with the user's moving direction data acquired from the gyro sensor of the earphone paged through the Bluetooth communicating unit 712 on the basis of the search path information to the specific destination provided from the route guidance service server to the user terminal.

Additionally, under the control of the controlling unit 718, the guidance sound controlling unit 720 controls the guidance sound so that the result of comparison with the user's moving direction data on the basis of the search path information corresponds to the cycle determined according to the rotation angle for each type of direction shifting position to selectively output the guidance sound to the left side or right side of the earphone.

In this case, the output cycle of the guidance sound is controlled correspondingly depending on whether the predetermined rotation angle exceeds the threshold through the guidance sound controlling unit. When the rotation angle exceeds a threshold, the guidance sound is continuously output at a predetermined short cycle to either a left side or right side of an earphone. When the rotation angle is below the threshold, the guidance sound is continuously output at a predetermined long cycle to the side opposite the side of the case of exceeding the threshold.

Furthermore, the wireless communicating unit 724 modulates a sine wave signal generated as the power is applied according to the input of the user's driving signal, amplifies the modulated signal into a required power level, and outputs the signal to at least one surrounding wireless communication equipment through a predetermined frequency.

The operation on the method and system for providing route guidance service for visually impaired people according to the present invention may be performed. Meanwhile, the present invention explained specific embodiments, but various modifications may be carried out without departing from the scope of the present invention. Thus, the scope of the present invention should be determined not based on the embodiments explained, but by the claims and equivalents to the claims.

What is claimed is:

1. A method for providing a route guidance service for visually impaired people, the method comprising the steps of:
when a predetermined application is selected through a user input, transmitting a request for a route guidance service together with location information acquired through the GPS of a user terminal simultaneously with execution of the selected application;
servicing, by a route guidance service server, search path information corresponding to an input destination on the basis of the location information received from the user terminal according to the route guidance service request from the user terminal;
broadcasting, by the user terminal, an inquiry signal through a Bluetooth device search request, identifying an earphone by a device which transmits a response signal to the broadcasted inquiry signal, and performing paging with the identified earphone; and
recognizing a user's walking direction on the basis of the search path information through outputting a signal by gyro sensors attached to both sides of the earphone according to a user's movement, converting the recognized result into a guidance sound according to a route guidance service rule, and outputting the guidance sound to the earphone,
wherein the recognized result is acquired by comparison with user's moving direction data acquired from a gyro sensor of an earphone paged through a Bluetooth communication based on search path information to a specific destination provided from the route guidance service server to a user terminal,
wherein the method is characterized by controlling the guidance sound as shown in the following equation so that the comparison result with the user's moving direction data corresponds to a predetermined cycle according to the rotation angle for each type of direction shifting position on the basis of the search path information to selectively output the guidance sound to a left side or right side of the earphone, $$N(\text{Hz}) = roundn\left(\frac{\Theta}{10}\right),$$

wherein an output cycle of the guidance sound is controlled correspondingly depending on whether a predetermined rotation angle exceeds a threshold, so that, when the rotation angle exceeds the threshold, the guidance sound is continuously output at a predetermined short cycle to either a left side or right side of an earphone, and when the rotation angle is below the threshold, the guidance sound is continuously output at a predetermined long cycle to the side opposite the side of the case of exceeding the threshold.

2. The method of claim 1, wherein the type of direction shifting position comprises nodes branched into at least two present on a travelling path where direction shifting occurs during route guidance service.

3. A method for providing a route guidance service for visually impaired people, the method comprising the steps of:
when a predetermined application is selected through a user input, transmitting a request for a route guidance service together with location information acquired through the GPS of a user terminal simultaneously with execution of the selected application;
servicing, by a route guidance service server, search path information corresponding to an input destination on the basis of the location information received from the user terminal according to the route guidance service request from the user terminal;
broadcasting, by the user terminal, an inquiry signal through a Bluetooth device search request, identifying an earphone by a device which transmits a response signal to the broadcasted inquiry signal, and performing paging with the identified earphone; and
recognizing a user's walking direction on the basis of the search path information through outputting a signal by gyro sensors attached to both sides of the earphone according to a user's movement, converting the recognized result into a guidance sound according to a route guidance service rule, and outputting the guidance sound to the earphone,
wherein the application has a plurality of divided areas, displays a menu item list in which the corresponding item is formed in each of the divided areas, sets a link to a relevant providing the service related with the item formed in the divided areas, and moves a screen to the page link set when selecting the corresponding menu item to provide the predetermined service,
wherein when a user interrupt occurs by exceeding the predetermined time at a specific area among the areas in which the menu item list is marked, a driving mode of the user terminal is converted into the mode for non-visually impaired people, and performs a menu service corresponding to the converted mode.

4. A system for providing a route guidance service for visually impaired people, the system comprising:
a user terminal which transmits, when a predetermined application is selected through a user input, a request for a route guidance service together with location information acquired through the GPS of a user terminal simultaneously with execution of the selected application;
a route guidance service server which services search path information corresponding to an input destination on the basis of the location information received from the user terminal according to the route guidance service request from the user terminal; and
an earphone which transmits a response signal to the broadcasted inquiry signal through a Bluetooth device search request at the user terminal, performs paging with the user terminal, and senses and outputs a user's movement through gyro sensors attached to both sides thereof,
wherein the user terminal comprises a controlling unit which recognizes a user's walking direction on the basis of the search path information through the gyro sensor of the earphone paged through the Bluetooth communication, adaptively coverts the recognized result into a guidance sound according to a route guidance service rule, and outputs the guidance sound to the earphone,
wherein under the control of the controlling unit, the user terminal controls the guidance sound so that the result of comparison with the user's moving direction data on the basis of the search path information corresponds to the cycle determined according to the rotation angle for each type of direction shifting position to selectively output the guidance sound to the left side or right side of the earphone, wherein the output cycle of the guidance sound is controlled correspondingly depending on whether the predetermined rotation angle exceeds the threshold, so that, when the rotation angle exceeds the threshold, the guidance sound is continuously output at a predetermined short cycle to either a left side or right side of an earphone, and when the rotation angle is below the threshold, the guidance sound is continuously output at a predetermined long cycle to the side opposite the side of the case of exceeding the threshold.

5. The system of claim 4, wherein the user terminal acquires the recognized result by performing a comparison through the comparing unit with the user's moving direction data acquired from the gyro sensor of the earphone paged through the Bluetooth communicating unit on the basis of the search path information to the specific destination provided from the route guidance service server to the user terminal.

* * * * *